(12) United States Patent
Williams

(10) Patent No.: US 7,479,664 B2
(45) Date of Patent: Jan. 20, 2009

(54) FIBER OPTIC PHOTOTHERAPY DEVICES INCLUDING LED LIGHT SOURCES

(75) Inventor: Jeffrey B. Williams, Hudson, OH (US)

(73) Assignee: Lumitex Inc., Strongsville, OH (US)

( * ) Notice: Subject to any disclaimer, the term of this patent is extended or adjusted under 35 U.S.C. 154(b) by 0 days.

(21) Appl. No.: 11/851,616

(22) Filed: Sep. 7, 2007

(65) Prior Publication Data

US 2007/0297141 A1    Dec. 27, 2007

Related U.S. Application Data

(62) Division of application No. 10/919,884, filed on Aug. 17, 2004, now Pat. No. 7,305,163.

(51) Int. Cl.
*H01L 33/00* (2006.01)
*G02B 6/26* (2006.01)

(52) U.S. Cl. ............... 257/98; 385/45; 385/78; 606/16

(58) Field of Classification Search ........... 257/98, 257/99, 100, E33.058, E33.067, E33.071, 257/E33.075; 385/45, 78, 89, 92, 901; 606/15, 606/16

See application file for complete search history.

(56) References Cited

U.S. PATENT DOCUMENTS

| | | | |
|---|---|---|---|
| 5,042,900 | A | 8/1991 | Parker |
| 5,339,223 | A | 8/1994 | Kremenchugsky et al. |
| 5,568,964 | A | 10/1996 | Parker et al. |
| 6,030,089 | A | 2/2000 | Parker et al. |
| 6,290,713 | B1 | 9/2001 | Russell |

*Primary Examiner*—Minh-Loan T Tran
(74) *Attorney, Agent, or Firm*—Renner, Otto, Boisselle & Sklar, LLP

(57) ABSTRACT

Fiber optic phototherapy devices include fiber optic light emitters having fiber optic end portions at one or both ends that may be separated into a plurality of groups of end portions that receive light from one or more light emitting diodes (LEDs). Lenses may be used to focus the light from one or more LEDs onto the end portions. The LEDs may be mounted to a heat sink to dissipate any excess heat generated by the LEDs.

17 Claims, 5 Drawing Sheets

FIBER OPTIC PHOTOTHERAPY DEVICES INCLUDING LED LIGHT SOURCES

CROSS-REFERENCE TO RELATED APPLICATIONS

This application is a division of U.S. patent application Ser. No. 10/919,884, filed Aug. 17, 2004.

FIELD OF THE INVENTION

This invention relates to phototherapy devices including fiber optic light emitters that receive light from one or more light emitting diodes (LEDs).

BACKGROUND OF THE INVENTION

Phototherapy has long been used to treat various known conditions including, for example, jaundice in newborn infants. Jaundice is caused by a build up of bilirubin in the blood of infants. Exposing the infant's skin to certain types of light will quickly reduce the bilirubin to a safe level. Such treatment is generally only needed for a few days, until the infant's liver is mature enough to process the bilirubin.

One type of phototherapy device that is commonly used in phototherapy treatment comprises a fiber optic light emitter having fiber optic end portions that receive light from a halogen lamp or other relatively high wattage light source to obtain the desired amount of light output from the light emitter. The problem with using relatively high wattage lamps as the light source is that they are not very efficient and produce large amounts of heat that require the use of a fan to cool the light source. Incorporating a fan into the light source makes the light source quite noisy during operation and substantially increases the overall cost and size of the light source. Also such relatively high wattage lamps typically have a relatively short life and provide less light over time.

A need thus exists for a fiber optic phototherapy device that may be lighted by a light source that requires considerably less wattage to operate while still producing substantially the same amount of light output from the fiber optic light emitter for a given unit surface area.

A need also exists to be able to selectively light different segments or areas of a fiber optic light emitter at the same or different times as desired to allow the light to be turned off to different segments or areas if not needed. This not only saves on power, but may also reduce the amount of light to which care providers are exposed. Some care providers are very sensitive to certain bands of light, particularly blue bands which are especially effective for phototherapy treatment. By cutting down on the amount of light from the light emitter to which the care provider may be exposed, there will be less stress on the care provider caused by light exposure.

SUMMARY OF THE INVENTION

The present invention relates to phototherapy devices including fiber optic light emitters having optical fiber end portions at one or both ends that receive light from one or more light emitting diodes (LEDs) for transmission of the light to the light emitters for emission therefrom.

In accordance with one aspect of the invention, the light from one or more LEDs is focused on the optical fiber end portions at one or both ends of the light emitters for transmission of the light to the light emitters.

In accordance with another aspect of the invention, one or more lenses may be used to focus the light from the LEDs on the optical fiber end portions.

In accordance with another aspect of the invention, the LEDs may be mounted on a heat sink to dissipate any excess heat generated by the LEDs.

In accordance with another aspect of the invention, the optical fiber end portions may be randomly mixed together and separated into a plurality of groups of end portions that receive light from a plurality of LEDs to provide a more uniform light output distribution from the light emitters.

In accordance with another aspect of the invention, the optical fiber end portions of different segments or areas of fiber optic light emitters may be grouped together in different groups and lighted by different light sources that may be selectively lighted for selectively lighting one or more of the segments or areas of the light emitters at the same or different times as desired.

In accordance with another aspect of the invention, LEDs having different bands of light may be focused on the same or different groups of optical fiber end portions of fiber optic light emitters.

In accordance with another aspect of the invention, the fiber optic light emitters may have optical fiber end portions extending from both ends of the light emitters that are mixed together for lighting both ends using one or more light sources.

In accordance with another aspect of the invention, the amount of power applied to the LEDs may be increased in accordance with a preprogrammed power curve based on an average life curve of the LEDs as the LEDs age over time or in response to a decrease in the light output from the LEDs to maintain a substantially constant light output from the LEDs over time.

These and other objects, advantages, features and aspects of the present invention will become apparent as the following description proceeds.

To the accomplishment of the foregoing and related ends, the invention, then, comprises the features hereinafter more fully described and particularly pointed out in the claims, the following description and the annexed drawings setting forth in detail certain illustrative embodiments of the invention, these being indicative, however, of but several of the various ways in which the principles of the invention may be employed.

DETAILED DESCRIPTION OF THE INVENTION

Figure 1:
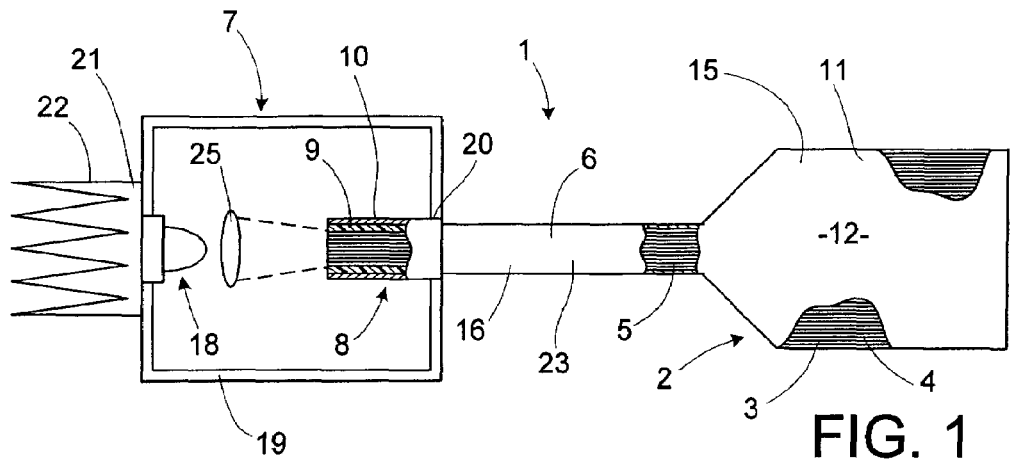
FIG. 1 is a schematic top plan view, partly in section, of one form of fiber optic phototherapy device of the present invention.

Referring now in detail to the drawings, and initially to FIG. 1, there is shown one form of phototherapy device 1 in accordance with this invention for use during phototherapy treatment of a patient including a fiber optic light emitting member 2 having one or more layers 3 of individual optical fibers 4 arranged in close proximity to each other. Each optical fiber includes a light transmitting core portion of a suitably optically transparent material and an outer sheath of a second optically transparent material having a different index of refraction than the core material to prevent the escape of light along its length. The core material may either be made of glass or plastic or a multi-strand filament having the desired optical characteristics. The outer sheath material is also optically transparent, but because its index of refraction is different than that of the core material, substantially total internal reflection is obtained at the sheath-core interface, as well known in the art.

Optical fibers 4 may extend beyond one or both ends of light emitter 2 where they may be bundled into one or more groups of optical fiber end portions 5 to form one or more light cables 6 for transmitting light from a remote light source 7 to the light emitter as described hereafter. In FIG. 1 the optical fibers are shown extending outwardly beyond one end only of the light emitter and bundled together to form a single light cable 6. At the outermost end of the light cable 6 is a connector assembly 8 which may consist of a suitable buffer material 9 surrounding the gathered optical fiber end portions and a ferrule 10 crimped onto the buffer material which squeezes the buffer material and packs the optical fiber end portions substantially solid.

Light emitter 2 is generally in the shape of a relatively thin light panel 11 having a greater width than thickness and opposite ends and sides and top and bottom surfaces, giving the light emitter increased flexibility. The light emitting surface 12 of the light panel 11 is typically larger than the cross-sectional area of the light cable to reduce energy density by spreading the light over a larger surface area at the light emitting surface.

A protective cover 15 made of a suitable flexible translucent or transparent material may surround the light emitter. Also a protective sleeve 16 made of a suitable flexible opaque or reflective material may surround light cable 6 for easy maneuverability to facilitate connection of the connector assembly 8 or other suitable attachment device at the outer end of the light cable to a remote light source 7 for transmission of the light through the light cable to the light emitter in a manner well known in the art. Suitable filters (not shown) may also be interposed between the light receiving end of the light cable and light source 7 to filter out any undesired frequencies of light, for example, infrared or ultraviolet, allowing only those light frequencies desired to pass through the light cable.

To cause light that is transmitted to light emitter 2 by light cable 6 to be emitted from the light emitter, the cladding on the outer surface of the optical fibers may be disrupted as by marring, abrading, scratching or otherwise causing mechanical, chemical or other disruptions at one or more areas along the length and width of the light emitter. The amount of light emitted at these locations is a function of the depth, size and/or frequency of such disruptions. For example, if the disruptions on the outer surface of the optical fibers are made larger and/or deeper and/or closer together as the distance from the light receiving end of the light emitter increases, there will be more uniform emission of light from the light emitter.

A suitable back reflector (shown at 17 in FIG. 6), made for example of Mylar or other suitable light reflective material, may be adhered to the back side of the light emitter for reflecting any light directed toward the back side back out the front side to provide illumination during phototherapy treatment.

Figure 2:
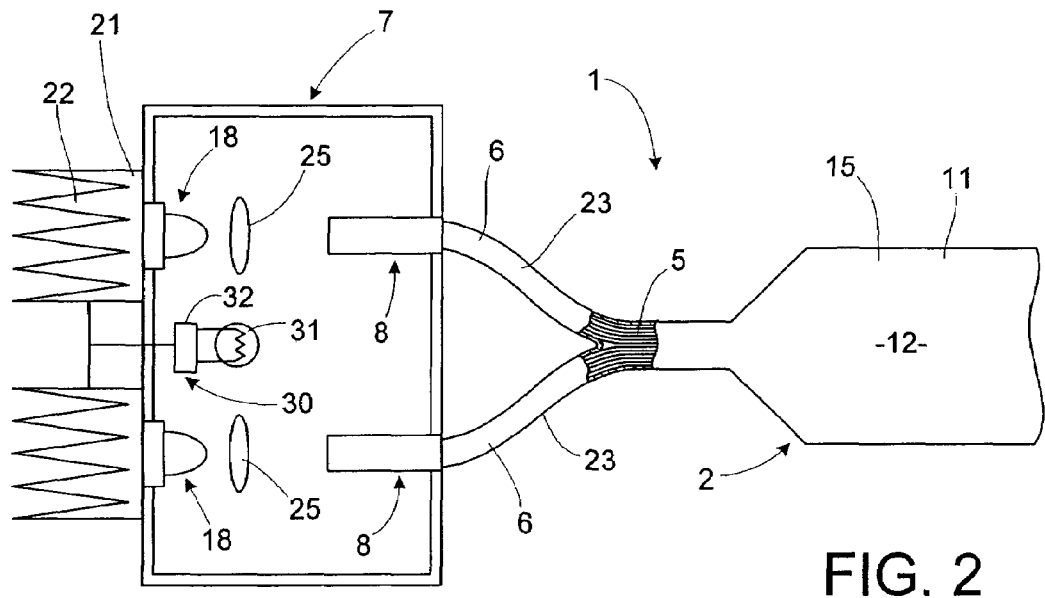
FIGS. 2-5, 7 and 8 are schematic top plan views, partly in section, of other forms of fiber optic phototherapy devices of the present invention.

Light source 7 may comprise one or more light emitting diodes (LEDs) 18 (including organic light emitting diodes (OLEDs) and poly light emitting diodes (PLEDs)) suitably mounted inside a housing 19. Light from the LEDs is focused on the outermost ends of light cables 6 whose connectors 8 extend into the housing through one or more openings 20 in the housing. FIG. 1 shows one such LED 18 mounted inside housing 19 with its light focused on the outermost end portion of one light cable 6 extending into the housing through opening 20 in alignment with the LED, whereas FIG. 2 shows two such LEDs 18 for end lighting two light cables 6 extending into the housing.

The actual number of LEDs 18 within a given light source 7 may vary depending on the particular wattage output of the LEDs and the desired amount of light output to be emitted from the light emitter 2 per unit light emitting surface area 12. A quarter inch diameter connector type ferrule 10, which is typically used to bundle together 400 optical fiber end portions, is optimum for focusing light from an LED light source onto such bundled optical fiber end portions. If one watt LEDs are used as the light source, it has been found that twelve such LEDs can provide a unit area light output from a light emitter comprised of 4800 optical fibers that is equivalent to that produced using a 120 watt halogen lamp light source. Twelve such LEDs can optimally light 4800 optical fibers, e.g., 400 optical fiber end portions crimped together in each of twelve ferrule type connectors. Of course, if higher wattage LEDs are used as the light source, for example three watt LEDs instead of one watt LEDs, the number of LEDs needed to produce the same unit area light output would be considerably less.

From this it is apparent that it is much more efficient to use small LEDs as the light source instead of a single high wattage light source such as a halogen lamp. Also LEDs are much longer lasting than high wattage light sources, and have a more useful blue light band width for phototherapy treatment than high voltage light sources. Further, LED light sources do not require a fan to cool the light sources as do high wattage light sources, thus eliminating the noisiness of a fan during use and allowing the light source to be made much smaller than light sources using high wattage light sources. At most all that may be needed to dissipate any excess heat generated by the LEDs would be to mount the LEDs to a heat sink 21 which may be attached to the back side of the housing and may have fins 22 protruding therefrom to further dissipate the heat as schematically shown in the majority of the drawing figures.

Higher wattage LEDs, up to five watts each, are also available for use as a light source. However, these higher wattage LEDs have a wider light dispersion angle, making them more difficult to focus the light on the outermost ends of the optical fiber light cables.

Figure 4:
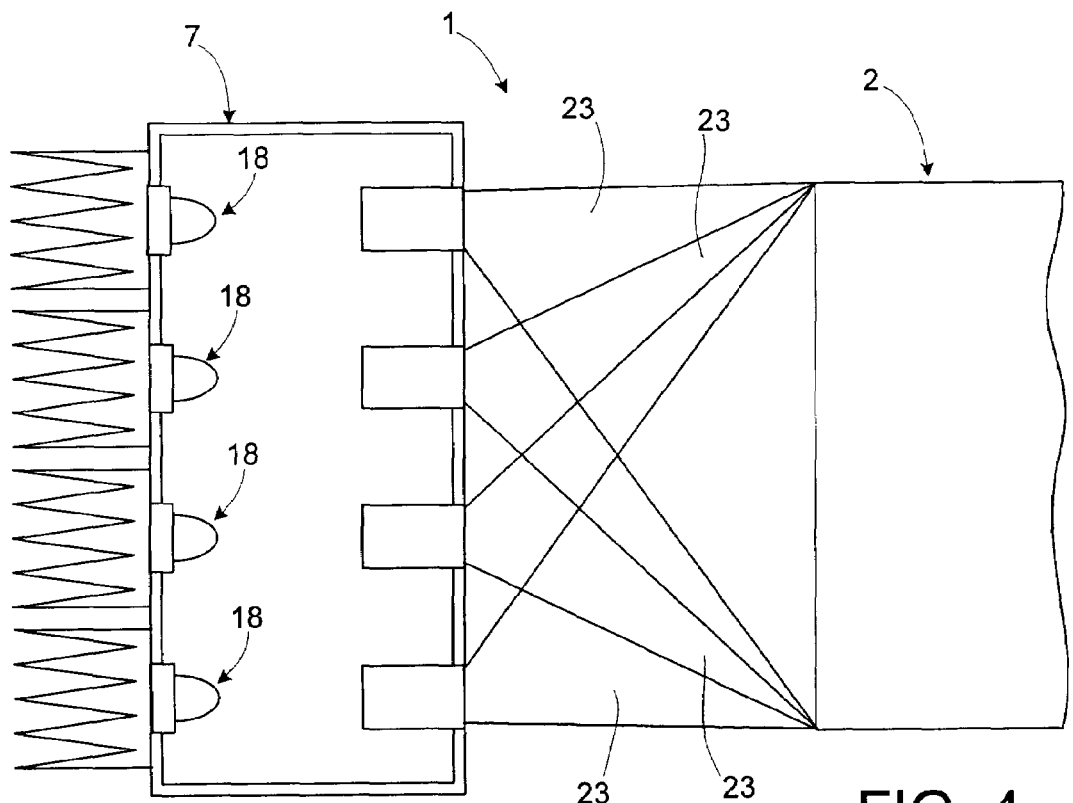

The optical fiber end portions 5 at one or both ends of a fiber optic light emitter 2 may be separated into more than one group 23 of end portions with the end portions of each group tightly secured together by ferrule type connectors 8 tightly surrounding the end portions of the respective groups for receiving light from one or more LEDs 18 as schematically shown in FIG. 2. Also the optical fiber end portions of a given light emitter 2 may be randomly mixed together prior to being separated into a plurality of groups 23 of optical fiber end portions as schematically shown in FIG. 4 to provide a more uniform light output distribution from the light emitter.

Figure 5:
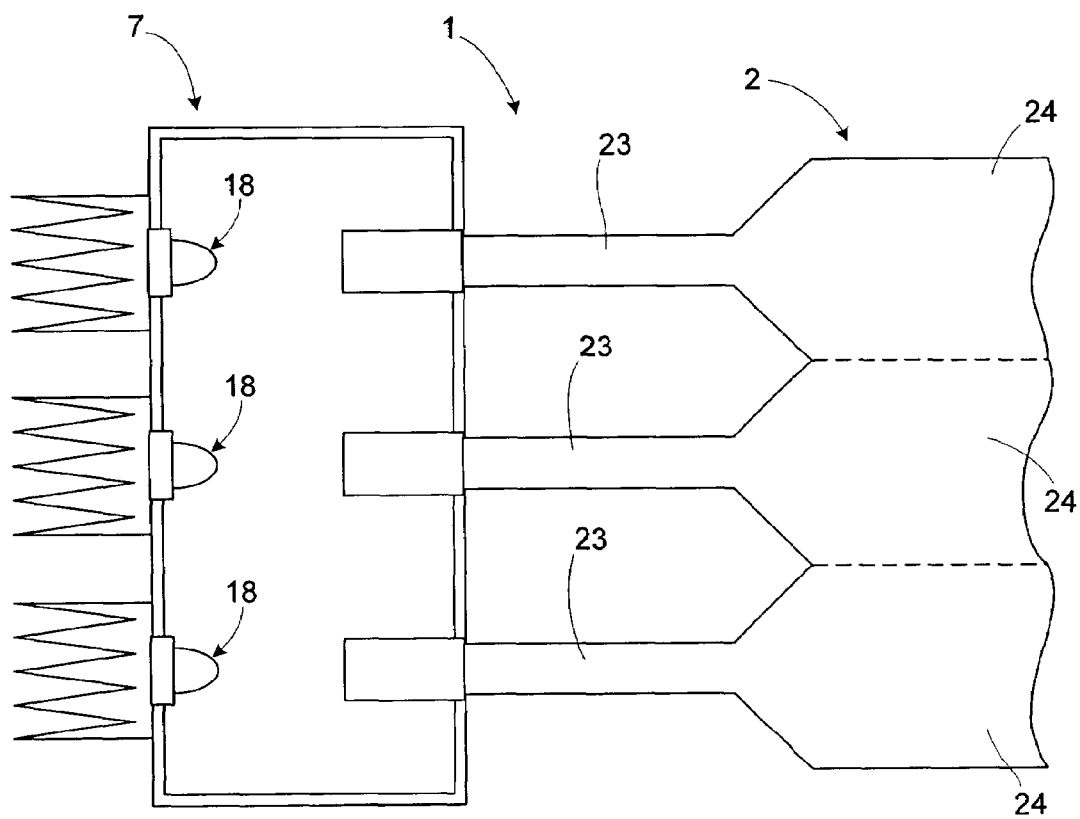

Further, the optical fiber end portions of different segments 24 of a light emitter 2 may each be grouped together in different groups 23 and the groups of optical fiber end portions for the different segments lighted by different LEDs 18 as schematically shown in FIG. 5 for selectively lighting any or all of the segments 24 of the light emitter at the same or different times as desired.

The advantage in being able to selectively light different segments or areas 24 of a fiber optic light emitter 2 is that it allows different segments of the light emitter to be turned off if not needed or if light is being wasted because of the relatively small surface area of a patient being subjected to phototherapy. Not only does this save on power, it also reduces the amount of light to which care providers may be exposed. Some individuals are very sensitive to certain bands of light, particularly blue bands which are especially effective for phototherapy. By cutting down on the amount of light from the light emitter that can be seen by the care provider, for example, when an infant receiving phototherapy treatment is placed on a relatively large/wide light emitter, there will be less stress on the care provider due to light exposure. Also the light output from LEDs 18 having different bands of light may be mixed with LEDs 18 having blue light bands in an attempt to reduce its effect on making some people nauseous.

Figure 3:
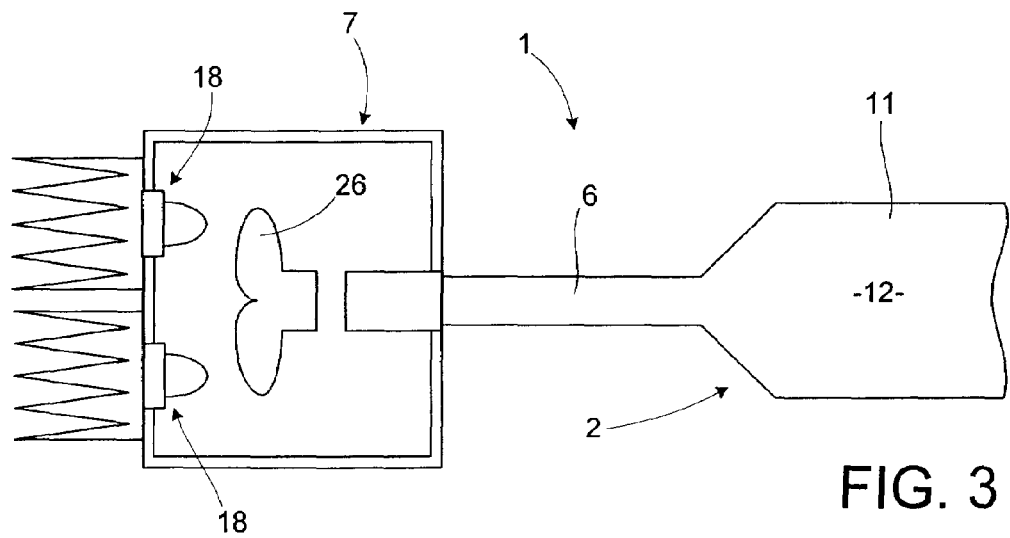

Suitable lenses may also be used to focus the light from one or more LEDs onto the outermost ends of the optical fiber light cables. FIGS. 1 and 2 schematically show lenses 25 for focusing light from a single light source onto one or more groups 23 of optical fiber end portions of a single light cable 6. Also, a multi-faceted lens 26 may be used to focus light from two or more LEDs 18 onto the optical fiber end portions of a single light cable 6 as schematically shown in FIG. 3.

Figure 6:
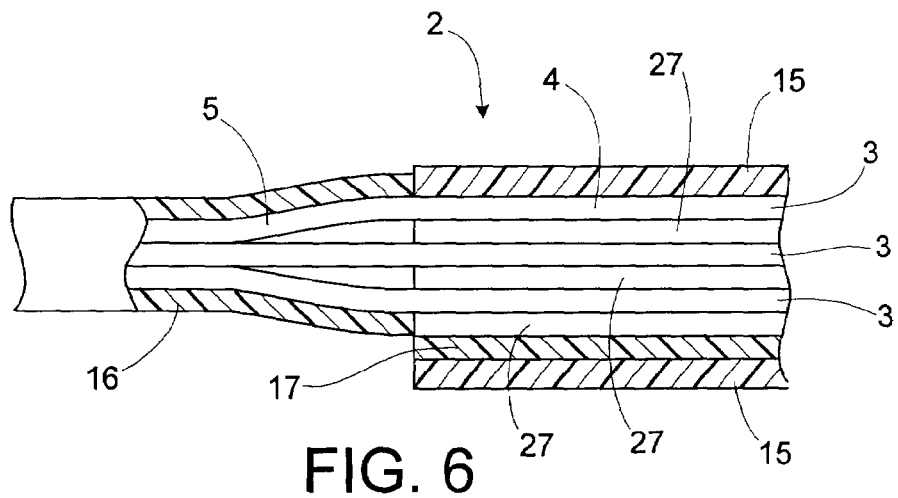
FIG. 6 is a schematic fragmentary longitudinal section showing one form of fiber optic light emitter of the fiber optic phototherapy devices of the present invention.
Figure 7:
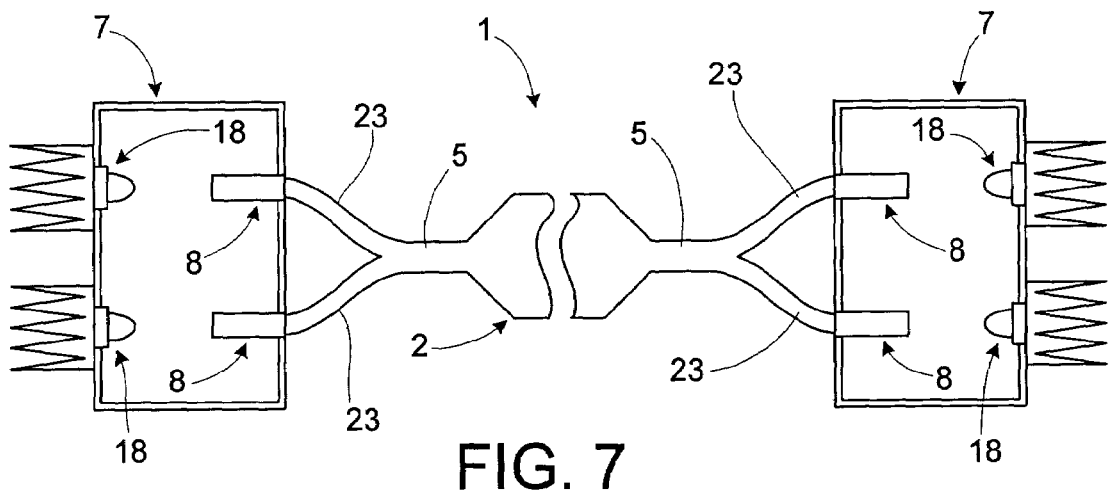
Figure 8:
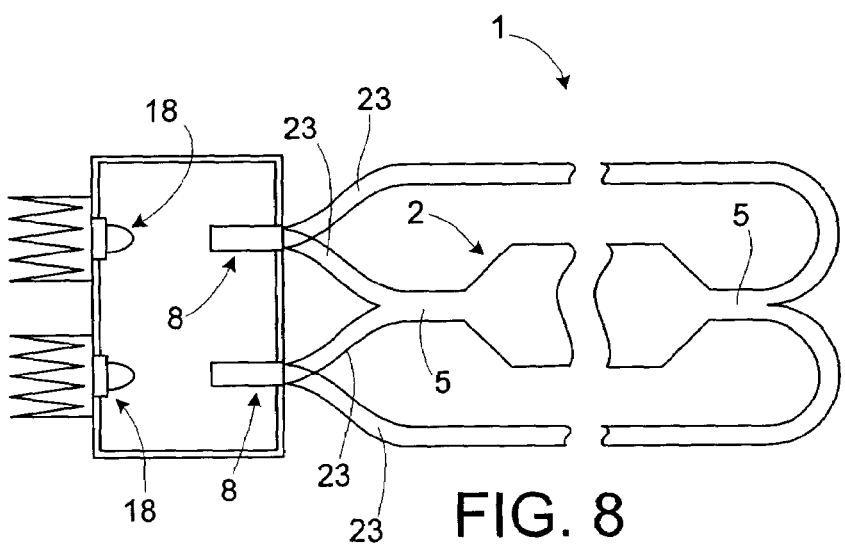

To increase the unit area light output from a given fiber optic light emitter, the light emitter may include plural layers 3 of optical fibers 4 as schematically shown in FIG. 6. Also the optical fibers 4 in each layer may have end portions 5 that are mixed together and grouped with the end portions of other layers as further schematically shown in FIG. 6 for producing a more uniform light output distribution from the light emitter. Further, the light emitters 2 may have fiber optic end portions extending from both ends of the light emitters that may be separated into a plurality of groups 23 of end portions and tightly secured together by ferrule type connectors 8 surrounding the fiber optic end portions of the respective groups for lighting by different LEDs 18 at both ends of the light emitter as schematically shown in FIG. 7. Alternatively, the optical fiber end portions at one end of the light emitter may be looped back and mixed with the optical fiber end portions at the other end of the light emitter for lighting both ends of the light emitter using the same LEDs 18 as schematically shown in FIG. 8.

Figure 9:
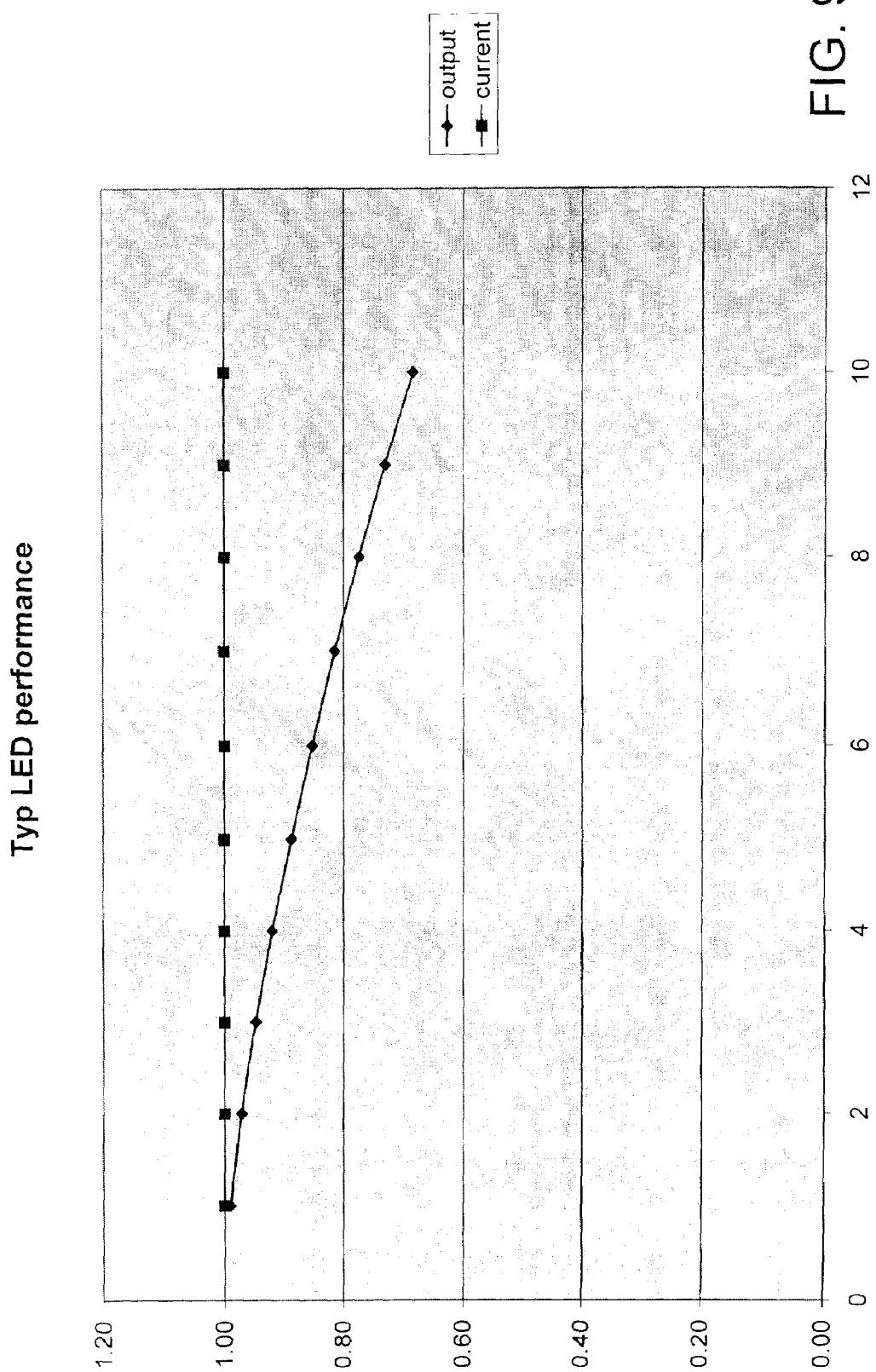
FIG. 9 is a schematic diagram of an average life curve of a population of light emitting diodes (LEDs)
Figure 10:
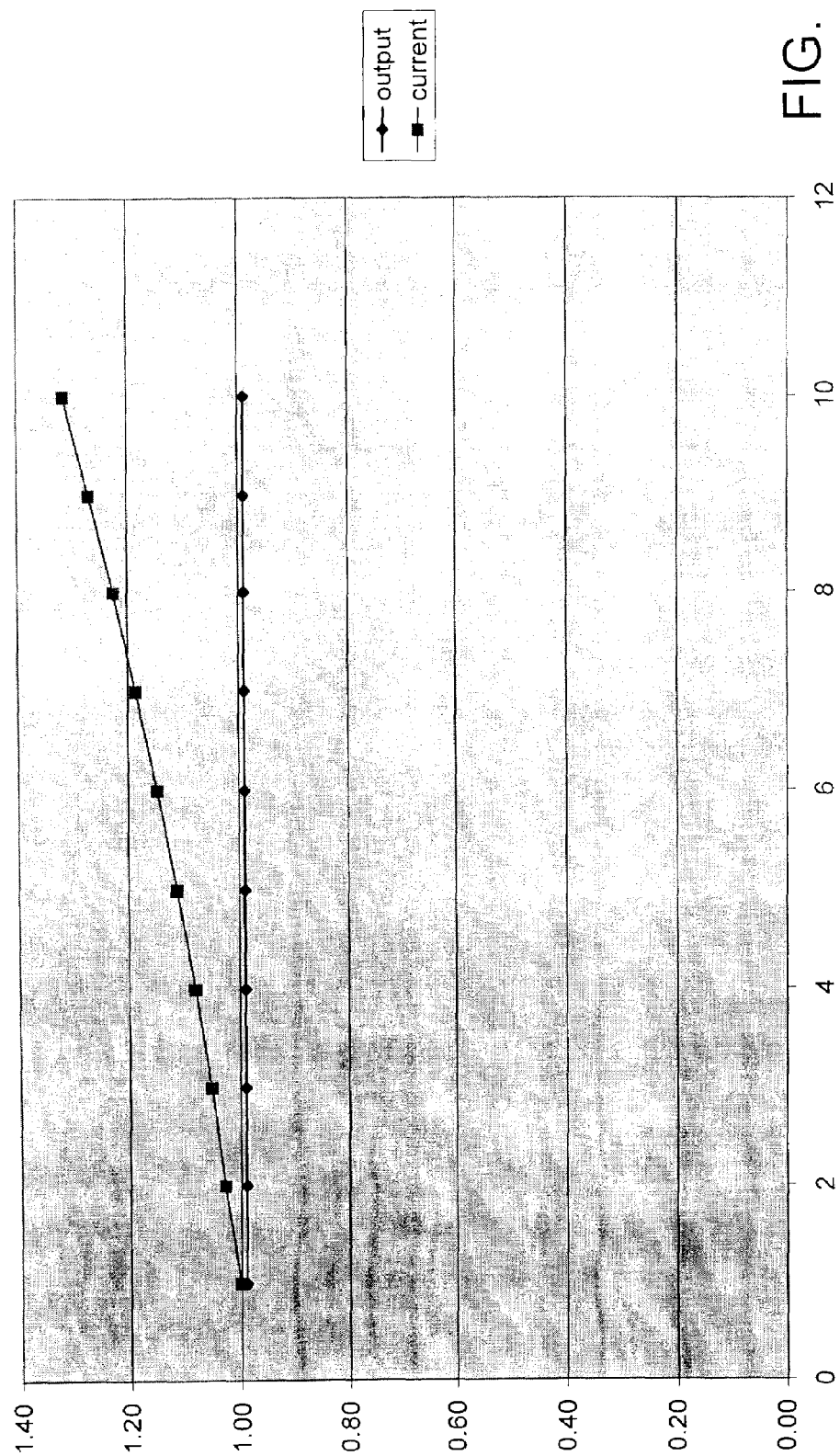
FIG. 10 is a schematic diagram of a preprogrammed power curve based on the average life curve of the LEDs of FIG. 9 that is used to increase the power to the LEDs as the LEDs age over time.

Over time the light output of the LEDs diminishes. To provide a more constant light output from a light emitter 2 over a longer period of time using LEDs as the light source, a feedback loop 30, schematically shown in FIG. 2, may be employed that includes a photocell 31 that detects the light output from the LEDs, and a circuit 32 that increases the power to the LEDs with decreased light output to maintain a substantially constant light output. The photocell 31 may be set up to detect stray light from the LEDs as schematically shown in FIG. 2 which is proportional to the light output from the LEDs. Alternatively, a preprogrammed power curve schematically shown in FIG. 10 based on an average light curve of the LEDs schematically shown in FIG. 9 may be used to increase the power (e.g., current) to the LEDs as the LEDs age over time.

Although the invention has been shown and described with respect to certain embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent) even though not structurally equivalent to the disclosed component which performs the functions in the herein exemplary embodiments of the invention. In addition, while a particular feature of the invention may have been disclosed with respect to only one embodiment, such feature may be combined with one or more other features of other embodiments as may be desired or advantageous for any given or particular application.

What is claimed is:

1. A phototherapy device for phototherapy treatment of a patient comprising a light emitter for emitting light, the light emitter comprising one or more layers of optical fibers, the optical fibers having end portions extending from at least one end of the light emitter, the end portions being tightly secured together, and at least one light emitting diode (LED) for focusing light on the end portions for transmission of the light to the light emitter for emission therefrom, wherein the at least one LED is inside a housing and is mounted to a heat sink attached to a back side of the housing to dissipate any excess heat generated by the at least one LED inside the housing.

2. The device of claim 1 further comprising a lens for focusing light from the at least one LED on the end portions.

3. The device of claim 1 wherein the light emitter includes a plurality of layers of optical fibers, the optical fibers of each layer having end portions that are mixed together and grouped with the end portions of other layers for producing a more uniform light output distribution from the light emitter.

4. The device of claim 1 wherein the optical fibers have end portions extending from both ends of the light emitter, and different light sources light the end portions at both ends of the light emitter.

5. The device of claim 1 further comprising fins protruding from the heat sink outwardly from the housing to further dissipate any excess heat generated by the at least one LED inside the housing.

6. The device of claim 1 wherein the optical fibers have end portions extending from both ends of the light emitter that are mixed together for lighting both ends of the light emitter using the same light source or light sources.

7. The device of claim 6 wherein a plurality of LEDs are used to light at least one group of mixed end portions of both ends of the light emitter.

8. The device of claim 6 wherein the end portions of both ends of the light emitter are randomly mixed together for producing a more uniform light output distribution from the light emitter.

9. The device of claim 1 wherein the light emitter has a greater width than thickness and is surrounded by a translucent or transparent protective cover.

10. The device of claim 1 wherein there are a plurality of LEDs for focusing light on the end portions, the light output of at least one of the LEDs having blue light bands, and the light output of at least one other LED having other color light bands that are selectively mixed with the blue light bands.

11. A phototherapy device for phototherapy treatment of a patient comprising a light emitter for emitting light, the light emitter comprising one or more layers of optical fibers, the optical fibers having end portions extending from at least one end of the light emitter, the end portions being tightly secured together, a plurality of light emitting diodes (LEDs) inside a housing for focusing light on the end portions for transmission of the light to the light emitter for emission therefrom, and a single multi-faceted lens inside the housing in close proximity to two or more LEDs for focusing light from the two or more LEDs onto the end portions.

12. The device of claim 11 wherein the LEDs are mounted to one or more heat sinks attached to a back side of the housing to dissipate any excess heat generated by the LEDs inside the housing.

13. The device of claim 12 further comprising fins protruding from the one or more heat sinks outwardly of the housing to further dissipate any excess heat generated by the LEDs inside the housing.

14. A phototherapy device for phototherapy treatment of a patient comprising a light emitter for emitting light, the light emitter comprising one or more layers of optical fibers, the optical fibers having end portions extending from at least one end of the light emitter, the end portions being tightly secured together, and at least one light emitting diode (LED) for focusing light on the end portions for transmission of the light to the light emitter for emission therefrom, the LED being mounted to a heat sink, and means for increasing the amount of power to a plurality of LEDs in response to a decrease in the light output from the LEDs to maintain a substantially constant light output from the LEDs.

15. The device of claim 14 wherein the means for increasing the amount of power to the LEDs comprises a photocell that detects light from the light source, and a circuit that increases the power to the LEDs as the light output from the LEDs decreases.

16. The device of claim 14 wherein the photocell detects stray light from the LEDs which is proportional to the light output from the LEDs.

17. A phototherapy device for phototherapy treatment of a patient comprising a light emitter for emitting light, the light emitter comprising one or more layers of optical fibers, the optical fibers having end portions extending from at least one end of the light emitter, the end portions being tightly secured together, and at least one light emitting diode (LED) for focusing light on the end portions for transmission of the light to the light emitter for emission therefrom, the LED being mounted to a heat sink, and a preprogrammed power curve based on an average life curve of a plurality of LEDs that is used to increase the power to the LEDs as the LEDs age over time.

* * * * *